(12) United States Patent
Lorenzon

(10) Patent No.: US 7,390,988 B2
(45) Date of Patent: Jun. 24, 2008

(54) POLYSPECIALISTIC MEDICAL-SURGICAL ELECTROWELDING METHOD FOR ELECTROWELDING TITANIUM AND ALLOYS THEREOF

(76) Inventor: Giorgio Lorenzon, Via della Resistenza, 31I-10032 Brandizzo (Torino) (IT)

( * ) Notice: Subject to any disclaimer, the term of this patent is extended or adjusted under 35 U.S.C. 154(b) by 0 days.

(21) Appl. No.: 11/087,020

(22) Filed: Mar. 22, 2005

(65) Prior Publication Data

US 2005/0205526 A1   Sep. 22, 2005

(30) Foreign Application Priority Data

Mar. 22, 2004   (IT) .......................... MI2004A0550

(51) Int. Cl.
  *B23K 11/10*   (2006.01)
  *B23K 11/16*   (2006.01)

(52) U.S. Cl. ........................ 219/118; 219/86.21; 219/74

(58) Field of Classification Search ................. 219/113, 219/111, 117.1, 118, 86.21, 90, 74
See application file for complete search history.

(56) References Cited

U.S. PATENT DOCUMENTS

| | | | | |
|---|---|---|---|---|
| 4,785,159 A | * | 11/1988 | Hruska | 219/111 |
| 5,168,917 A | * | 12/1992 | Okuda et al. | 164/495 |
| 5,334,016 A | * | 8/1994 | Goldsmith et al. | 433/29 |
| 6,099,520 A | * | 8/2000 | Shimoji | 606/2 |

\* cited by examiner

*Primary Examiner*—Kevin P Kerns
(74) *Attorney, Agent, or Firm*—James V. Costigan; Hedman & Costigan, P.C.

(57) ABSTRACT

The present invention relates to an electrowelding method for intraorally electrowelding titanium and alloys thereof, comprising the step of abutting the element to be electrowelded one against the other, performing an electrowelding operation by using an electrowelding current, cooling while holding a welding pressure, characterized in that said method provides to apply, at the welding zone, a set argon flow.

1 Claim, No Drawings

POLYSPECIALISTIC MEDICAL-SURGICAL ELECTROWELDING METHOD FOR ELECTROWELDING TITANIUM AND ALLOYS THEREOF

BACKGROUND OF THE INVENTION

The present invention relates to a method for intraorally electrowelding titanium and alloys thereof, which can also be applied to other medical-surgical procedures in other districts.

As is known, in intraorally electrowelding titanium and alloys thereof, which operation is performed by a syncrystallization method, it is necessary to apply a set pressure during the electrowelding operation proper.

In such an electrowelding method, a portion of the metal material affected by the welding can be subjected to a gauge loss, deriving from a degeneration of the surface layer because of the oxygen oxidating action.

This surface layer, in particular, is greatly affected through its thickness by the used current amount and it has been found that, in a case of a very high current, the surface oxidation may be such as to break away the welded elements, both immediately, and after a long time, because of a spoiling of the metallurgical properties of the titanium material.

SUMMARY OF THE INVENTION

Thus, the aim of the present invention is to overcome the above mentioned problems, by providing a method for intraorally electrowelding titanium and alloys thereof, allowing to operate in such an operating environment which does not cause any gauge losses of the parts subjected to a syncrystallization, thereby providing a better coupling of the elements.

Within the scope of the above mentioned aim, a main object of the present invention is to provide a titanium electrowelding method, in which the interpenetration of the hexagonal prisms forming the structure can be performed without structural alterations, thereby providing a much stronger mechanical binding, since the overall available mass is used.

According to one aspect of the present invention, the above mentioned aim and objects, as well as yet other objects, which will become more apparent hereinafter, are achieved by a method for intraorally electrowelding titanium and alloys thereof, comprising the steps of abutting the elements to be electrowelded, performing an electrowelding by causing the passage of a current, cooling by holding a welding pressure, characterized in that said method further comprises the step of applying, at the welding zone, a set argon flow.

DESCRIPTION OF THE PREFERRED EMBODIMENTS

Further characteristics and advantages of the present invention will become more apparent from the following disclosure of a method for intraorally electrowelding titanium and alloys thereof, which will be illustrated in the following disclosure.

More specifically, the electrowelding method for intraorally electrowelding titanium and alloys thereof, is an autogenous electrowelding method, in which the base metal intervenes by syncrystallization in the construction of the welded joint.

In actual practice, the syncrystallization provides the joining of two metal surfaces by associating atoms in the structure of the crystalline grid of the joining zone.

To provide the above mentioned syncrystallization, it is necessary to apply a set mechanical pressure, and provide a welding current adapted to provide, by a joule effect, the welding heat.

In the welding method, the welding is obtained by a high intensity current, jointly with a mechanical pressure to be applied on the surfaces to be welded, which are held in a close contact one against the other.

Advantageously, the pressure is applied for a time longer than that in which the current passes, since the pressure cycle is started before and ended after the current cycle, owing to the fact that, at the start, the elements to be welded are abutted against one another, and during this abutment a currentless pressure is applied.

Then, the welding step proper with a simultaneous application of the pressure and current up to the melting of the core is carried out.

Then is performed a cooling step, in which no current is used, the pressure being however held at a set value.

To solve the above mentioned problem, it has been found that the oxidation phenomenon on the involved surfaces is drastically eliminated, if a set argon flow is caused to impinge on the welding electrodes applied on the system and the coupling bar.

By applying argon inside the oral cavity, an argon saturated microenvironment is generated, allowing to provide a stable and accurate joining of the elements being processed.

In the presence of argon, accordingly, the interpenetration of the hexagonal prisms constituting the structure is obtained without structural alterations, thereby providing a very strong mechanical binding affecting the overall available mass.

In carrying out the method, no surface oxidation phenomenon susceptible to negatively affect the quality of the constructions to be joined occurs.

Another important aspect of the invention is that the argon gas is not dangerous for the human being, since it is present in nature.

This gas, moreover, is broadly used in the medical field for different specialistic diagnostic and operating branches.

From the above disclosure it should be apparent that the invention fully achieves the intended aim and objects.

In fact, the invention provides a method for intraorally electrowelding titanium, in which no oxidation of the surface is being processed occurs, thereby providing optimum electrowelding results.

The invention, as disclosed, is susceptible to several modifications and variations, all of which will come within the scope of the invention, which can be extended and applied to other specialistic application (for example in orthopedy).

Moreover, all of the constructional details can be replaced by other technically equivalent elements and solutions.

In practicing the invention, the used materials, as well as the contingent size and shapes, can be any, depending on requirements.

The invention claimed is:

1. A method for intraorally electrowelding titanium and alloys thereof in an oral cavity of a patient, comprising the steps of abutting, by applying mechanical pressure thereon, first and second hexagonal prism elements to be electrowelded, applying an argon flow at said first and second abutted prism elements to be electrowelded, causing an electric current to flow through said first and second abutted prism elements while continuing to apply said mechanical pressure and electowelding said first and second abutted prism elements, switching off the electric current when said first and second prism elements have been electrowelded to one another by penetrating one another to form a strong mechanical bond and thereafter cooling said first and second electrowelded prism elements while continuing to apply mechanical pressure.

* * * * *